US00PP26216P2

(12) United States Plant Patent
Hoekert

(10) Patent No.: US PP26,216 P2
(45) Date of Patent: Dec. 15, 2015

(54) ***CALLUNA* PLANT NAMED 'K6322'**

(50) Latin Name: *Calluna vulgaris*
Varietal Denomination: K6322

(71) Applicant: Hendrick Cozijn Hoekert, Wezep (NL)

(72) Inventor: Hendrick Cozijn Hoekert, Wezep (NL)

(73) Assignee: Eden's Creations B.V., Oldebroek (NL)

( * ) Notice: Subject to any disclaimer, the term of this patent is extended or adjusted under 35 U.S.C. 154(b) by 191 days.

(21) Appl. No.: 13/998,437

(22) Filed: Oct. 31, 2013

(51) Int. Cl.
*A01H 5/12* (2006.01)

(52) U.S. Cl.
USPC ..... Plt./231

(58) Field of Classification Search
USPC ..... Plt./231
See application file for complete search history.

*Primary Examiner* — Anne Grunberg
(74) *Attorney, Agent, or Firm* — C. A. Whealy

(57) ABSTRACT

A new and distinct cultivar of *Calluna* plant named 'K6322', characterized by its compact and upright to outwardly spreading plant habit; freely basal and lateral branching habit; dense and bushy appearance; moderately vigorous growth habit; thick squarish branches; green-colored leaves that become light yellow in color during the autumn and winter; and good garden performance.

1 Drawing Sheet

Botanical designation: *Calluna vulgaris.*
Cultivar denomination: 'K6322'.

CROSS REFERENCED TO CLOSELY-RELATED APPLICATIONS

Title: *Calluna* Plant Named 'K6300'
Applicant: Hendrick Cozijn Hoekert
Filed: Concurrently with this application having application Ser. No. 13/998,438

BACKGROUND OF THE INVENTION

The present Invention relates to a new and distinct cultivar of *Calluna* plant, botanically known as *Calluna vulgaris* and hereinafter referred to by the name 'K6322'.

The new *Calluna* plant is a product of a planned breeding program conducted by the Inventor in Wezep, The Netherlands. The objective of the breeding program is to create new upright *Calluna* plants having thick squarish branches and attractive leaf color.

The new *Calluna* plant originated from a cross-pollination made by the Inventor in September, 2005 in Wezep, The Netherlands, of a proprietary selection of *Calluna vulgaris* identified as code number K5048, not patented, as the female, or seed, parent with a proprietary selection of *Calluna vulgaris* identified as code number E5025, not patented, as the male, or pollen, parent. The new *Calluna* plant was discovered and selected by the Inventor as a single plant within the progeny of the stated cross-pollination in a controlled greenhouse environment in Wezep, The Netherlands in September, 2006.

Asexual reproduction of the new *Calluna* plant by cuttings taken in a controlled greenhouse environment in Wezep, The Netherlands since September, 2006 has shown that the unique features of this new *Calluna* plant are stable and reproduced true to type in successive generations.

SUMMARY OF THE INVENTION

Plants of the new *Calluna* have not been observed under all possible environmental conditions and cultural practices. The phenotype may vary somewhat with variations in environmental conditions such as temperature and light intensity without, however, any variance in genotype. The following traits have been repeatedly observed and are determined to be the unique characteristics of 'K6322'. These characteristics in combination distinguish 'K6322' as a new and distinct *Calluna* plant:

1. Compact and upright to outwardly spreading plant habit.
2. Freely basal and lateral branching habit; dense and bushy appearance; moderately vigorous growth habit.
3. Thick squarish branches.
4. Green-colored leaves that become light yellow in color during the autumn and winter.
5. Good garden performance.

Plants of the new *Calluna* differ primarily from plants of the female parent selection in the following characteristics:

1. Plants of the new *Calluna* are more uniform than plants of the female parent selection.
2. Plants of the new *Calluna* have thicker branches than plants of the female parent selection.

Plants of the new *Calluna* differ primarily from plants of the male parent selection in the following characteristics:

1. Plants of the new *Calluna* have squarish branches whereas plants of the male parent selection have round branches.
2. Leaves of plants of the new *Calluna* become light yellow in color during the autumn and winter whereas leaves of plants of the male parent selection do not change color during the autumn and winter.

Plants of the new *Calluna* can be compared to *Calluna vulgaris* 'K6300', disclosed in a U.S. Plant Patent application filed concurrently having application Ser. No. 13/998,438. In side-by-side comparisons, plants of the new *Calluna* differ from plants of 'K6300' in the following characteristics:

1. Plants of the new *Calluna* are shorter than plants of 'K6300'.
2. Plants of the new *Calluna* are not as freely branching as plants of 'K6300'.

3. Leaves of plants of the new *Calluna* become light yellow in color during the autumn and winter whereas leaves of plants of 'K6300' become greyed orange in color during the autumn and winter.

Plants of the new *Calluna* can be compared to the plants of *Calluna vulgaris* 'Nr 580', disclosed in U.S. Plant Pat. No. 20,530. In side-by-side comparisons conducted in Wezep, The Netherlands, plants of the new *Calluna* differed primarily from plants of 'Nr 580' in branch appearance as plants of 'Nr 580' had round branches.

Plants of the new *Calluna* can be compared to the plants of *Calluna vulgaris* 'Nr 5157', disclosed in U.S. Plant Pat. No. 20,529. In side-by-side comparisons conducted in Wezep, The Netherlands, plants of the new *Calluna* differed primarily from plants of 'Nr 5157' in branch thickness as plants of 'Nr 5157' had thinner branches than plants of the new *Calluna*.

Plants of the new *Calluna* can also be compared to the plants of *Calluna vulgaris* 'Nr 5163', disclosed in U.S. Plant Pat. No. 20,527. In side-by-side comparisons conducted in Wezep, The Netherlands, plants of the new *Calluna* differed primarily from plants of 'Nr 5163' in leaf color as leaves of plants of 'Nr 5163' did not change color during the autumn and winter.

BRIEF DESCRIPTION OF THE PHOTOGRAPH

The accompanying colored photograph illustrates the overall appearance of the new *Calluna* plant showing the colors as true as it is reasonably possible to obtain in colored reproductions of this type. Colors in the photograph may differ slightly from the color values cited in the detailed botanical description which accurately describe the colors of the new *Calluna* plant.

The photograph comprises a side perspective view of typical plant of 'K6322' grown in a container.

DETAILED BOTANICAL DESCRIPTION

The above-mentioned photograph and following observations and measurements describe plants grown during the summer and early autumn in 13-cm containers in an outdoor nursery in Wezep, The Netherlands and under cultural practices which approximate commercial *Calluna* production. During the production of the plants, day temperatures ranged from 14° C. to 27° C. and night temperatures ranged from 5° C. to 17° C. Plants were two years old when the photograph and the detailed description were taken. In the following description, color references are made to The Royal Horticultural Society Colour Chart, 2007 Edition, except where general terms of ordinary dictionary significance are used.

Botanical classification: *Calluna vulgaris* 'K6322'.

Parentage:

*Female, or seed, parent*.—Proprietary selection of *Calluna vulgaris* identified as code number K5048, not patented.

*Male, or pollen, parent*.—Proprietary selection of *Calluna vulgaris* identified as code number E5025, not patented.

Propagation:

*Type*.—By cuttings.

*Time to initiate roots, summer*.—About 30 days at temperatures about 20° C. to 25° C.

*Time to initiate roots, winter*.—About 60 days at temperatures about 20° C. to 25° C.

*Time to produce a rooted young plant, summer*.—About 50 days at temperatures about 20° C. to 25° C.

*Time to produce a rooted young plant, winter*.—About 70 days at temperatures about 20° C. to 25° C.

*Root description*.—Fine, fibrous; white in color.

*Rooting habit*.—Freely branching; dense.

Plant description:

*Plant form, plant and growth habit*.—Perennial evergreen subshrub; compact, upright to outwardly spreading plant habit; moderately vigorous growth habit.

*Branching habit*.—Freely basal and lateral branching habit with about 34 branches developing per plant; dense and bushy appearance.

*Plant height*.—About 17.6 cm.

*Plant diameter, area of spread*.—About 19.3 cm.

*Lateral branch description*.—Length: About 1 cm. Diameter: About 1 mm. Internode length: About 1 mm. Shape: Squarish appearance. Strength: Strong. Aspect: Upright to outwardly spreading. Texture: Smooth, glabrous. Color, developing: Close to 145A to 145B. Color, mature: Close to between 161A and 164D.

*Leaf description*.—Arrangement: Opposite; simple; sessile. Length: About 2 mm. Width: About 0.75 mm. Shape: Ovate. Apex: Obtuse. Base: Decurrent. Margin: Entire. Venation pattern: Pinnate; inconspicuous. Texture, upper and lower surfaces: Smooth, glabrous; luster, glossy. Color: Developing leaves, upper and lower surfaces: Close to 144B; towards the apex, close to 154C. Fully expanded leaves, upper and lower surfaces: Close to 154C to 154D; venation, close to 154C to 154D, during the autumn and winter, leaves become close to 3A to 3B in color.

Flower description: Flower initiation and development have not been observed on plants of the new *Calluna*.

Garden performance & temperature tolerance: Plants of the new *Calluna* have been observed to have good garden performance and to be tolerant to rain, wind and temperatures ranging from about −20° C. to about 35° C. Plants of the new *Calluna* are hardy to USDA Hardiness Zone 5.

Disease & pest resistance: Plants have not been observed to be resistant to pathogens and pests common to *Calluna* plants.

It is claimed:

1. A new and distinct cultivar of *Calluna* plant named 'K6322' as illustrated and described.

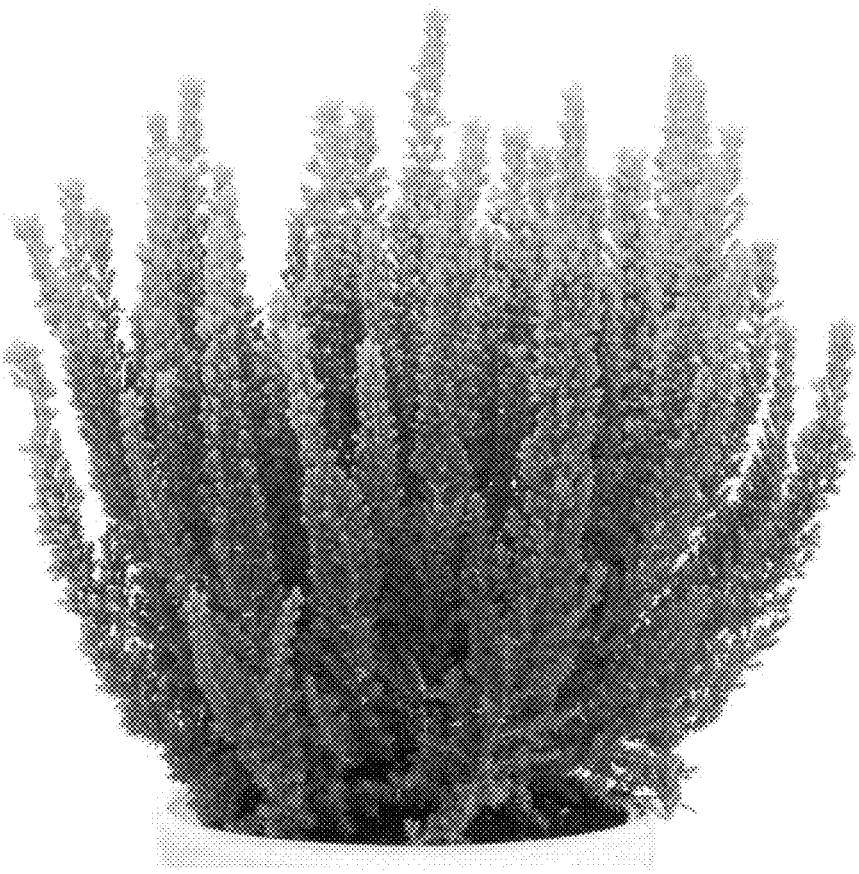

* * * * *